United States Patent [19]
Ellingson et al.

[11] Patent Number: 5,426,506
[45] Date of Patent: Jun. 20, 1995

[54] OPTICAL METHOD AND APPARATUS FOR DETECTION OF SURFACE AND NEAR-SUBSURFACE DEFECTS IN DENSE CERAMICS

[75] Inventors: William A. Ellingson, Naperville, Ill.; Mark P. Brada, Goleta, Calif.

[73] Assignee: The University of Chicago, Chicago, Ill.

[21] Appl. No.: 36,320

[22] Filed: Mar. 22, 1993

[51] Int. Cl.$^6$ .................... G01N 21/01; G01N 21/88
[52] U.S. Cl. .................................... 356/369; 250/225; 250/572
[58] Field of Search ............... 356/338, 369, 430, 237; 250/572, 562, 563, 225

[56] References Cited

U.S. PATENT DOCUMENTS

| | | | |
|---|---|---|---|
| 3,993,976 | 11/1976 | Ginsburg | 250/550 |
| 4,314,017 | 2/1982 | Takahashi et al. | 430/109 |
| 4,314,763 | 2/1982 | Steigmeier et al. | 356/237 |
| 4,352,016 | 9/1982 | Duffy et al. | 250/358.1 |
| 4,391,524 | 7/1983 | Steigmeier et al. | 356/338 |
| 4,933,567 | 6/1990 | Silva et al. | 356/369 |
| 4,978,862 | 12/1990 | Silva et al. | 356/369 |
| 5,032,734 | 7/1991 | Orazio, Jr. et al. | 250/572 |
| 5,070,045 | 12/1991 | Comte et al. | 501/4 |
| 5,196,716 | 3/1993 | Moriya et al. | 250/572 |

*Primary Examiner*—Robert Limanek
*Assistant Examiner*—David B. Hardy
*Attorney, Agent, or Firm*—Emrich & Dithmar

[57] ABSTRACT

A laser is used in a non-destructive manner to detect surface and near-subsurface defects in dense ceramics and particularly in ceramic bodies with complex shapes such as ceramic bearings, turbine blades, races, and the like. The laser's wavelength is selected based upon the composition of the ceramic sample and the laser can be directed on the sample while the sample is static or in dynamic rotate or translate motion. Light is scattered off surface and subsurface defects using a preselected polarization. The change in polarization angle is used to select the depth and characteristics of surface/subsurface defects. The scattered light is detected by an optical train consisting of a charge coupled device (CCD), or vidicon, television camera which, in turn, is coupled to a video monitor and a computer for digitizing the image. An analyzing polarizer in the optical train allows scattered light at a given polarization angle to be observed for enhancing sensitivity to either surface or near-subsurface defects. Application of digital image processing allows subtraction of digitized images in near real-time providing enhanced sensitivity to subsurface defects. Storing known "feature masks" of identified defects in the computer and comparing the detected scatter pattern (Fourier images) with the stored feature masks allows for automatic classification of detected defects.

17 Claims, 11 Drawing Sheets

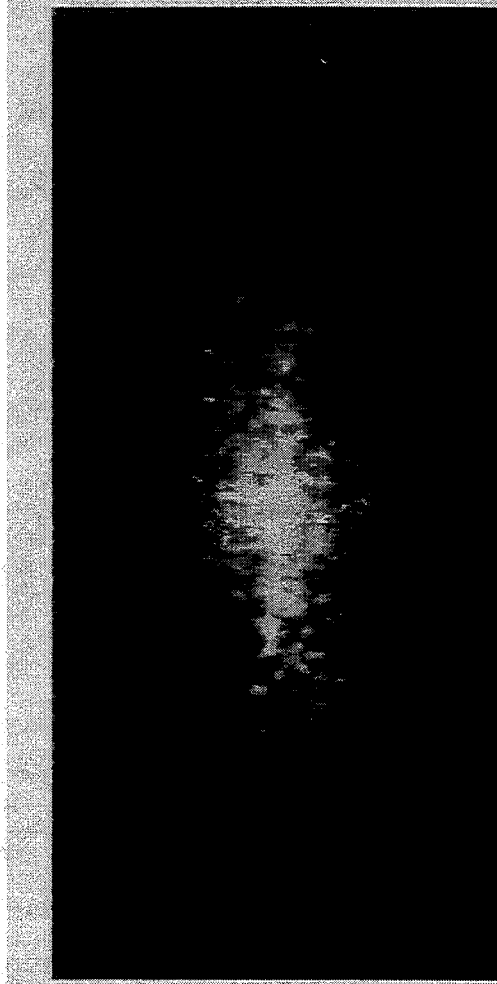
FIG. 10a  $R_a \approx 0.03$ μm
FIG. 10b  $R_a \approx 0.07$ μm No Defect Defect at 75 μm Defect at 102 μm

OPTICAL METHOD AND APPARATUS FOR DETECTION OF SURFACE AND NEAR-SUBSURFACE DEFECTS IN DENSE CERAMICS

CONTRACTUAL ORIGIN OF THE INVENTION

The United States Government has rights in this invention pursuant to Contract No. W-31-109-ENG-38 between the U.S. Department of Energy and The University of Chicago representing Argonne National Laboratory.

FIELD OF THE INVENTION

This invention relates generally to the detection of surface and near-subsurface defects in dense ceramics and is particularly directed to an optical method and apparatus for detecting surface and near-subsurface defects in ceramic bodies with complex shapes such as ceramic bearings, turbine blades, races, and the like.

BACKGROUND OF THE INVENTION

The useful lifetime of rolling contact fatigue elements such as bearings can be shortened significantly if the element is not free of surface or subsurface defects. Ceramic rolling elements, especially ball bearings, are rapidly being developed for commercial applications. Presently, because of their mechanical and physical properties, $Si_3N_4$ ceramics are preferred for use in ceramic rolling elements as they offer a number of advantages over steel counterparts. These advantages include higher stiffness, increased operating speeds, and improved corrosion resistance and thermal stability. In addition, the primary failure mode of $Si_3N_4$ bearings is by spallation, the least harmful mode of failure.

Ceramic bearings are typically classified into two types: (1) hybrid bearings which include a ceramic rolling element and steel races; or (2) all-ceramic bearings which have ceramic rolling elements and ceramic races. Machining operations are typically different for each type of ceramic component. Bearings are usually machined from hot pressed "blanks" which are then hot isostatically pressed (HIPped) and finally lapped to finishes on the order of <0.05 μm Ra. Races on the other hand are often ground with surface finishes of <0.1-0.2 μm Ra. These machining operations can potentially introduce surface and subsurface defects. However, subsurface defects could also be inherently present in the material and not effect machining while still having an adverse impact on useful lifetime. Non-destructive testing methods which can be reliably applied to map surface and near-subsurface defects in a production environment are therefore highly desirable.

One non-destructive characterization (NDC) method which has been extensively studied for metal surfaces (typically optical surfaces) is optical scattering. Optical scattering occurs whenever a beam of light is incident upon a surface. Fundamental geometric optics predicts that for a perfect reflector the angle of reflection will be equal to the angle of incidence. However, if the surface on which the light is incident is transparent, or semi-transparent, then a component of the beam will be internally transmitted (except at the critical angle). Certain $Si_3N_4$ ceramics are partially transparent at selected wavelengths. FIG. 1 is a simplified schematic diagram of an incident optical beam 11 on a partially transparent material 10. A reflected beam 12, a transmitted optical beam 14, scattered light 16 and various subsurface optical scatterers 18 are present. However, many features on a scattering surface, particularly a machined ceramic surface, can cause scatter. Some of these features are shown in simplified schematic diagram form in FIG. 2, which shows a range of surface roughness, surface particulate, cutting oils and subsurface defects of different shape, orientation and location.

A non-destructive method capable of discriminating between surface defects and subsurface defects is highly desirable. One common approach employs polarized laser light incident on the surface of the material being analyzed as shown in simplified schematic diagram form in FIG. 3. In FIG. 3, "P" represents P polarized light where the electric vector is parallel to the plane of incidence and "S" represents S polarized light where the electric vector is perpendicular to the plane of incidence. As shown in FIG. 3, a portion of the incident light is transmitted through the material and a portion is reflected as well as scattered from the surface of the material. The material under study is shown in the X-Y plane. For subsurface defect detection, surface scatter can be considered noise and subsurface scatter the signal. To improve the signal-to-noise (S/N) ratio one must either remove the surface effects for subsurface defect detection, or enhance surface topography scatter by removing subsurface scatter effects.

For all transparent dielectric materials, each of the two orthogonal polarizations (s and p) have different reflectivities. In addition, these reflectivities are a function of angle of incidence. One unique feature of this functionality is that for a given material there is a single angle, known as the Brewster angle, at which the reflectivity for p-polarized light is exactly zero. This means that by illuminating a specimen at its Brewster angle, the surface or subsurface may be predominantly examined by alternating the laser beam from s- to p-polarization, respectively. This Brewster angle is defined as $$\Theta_B = \arctan\left(\frac{n_t}{n_i}\right)$$

where $n_i$ is the refractive index of the incident medium (usually air) and $n_t$ is the index of the material itself. Most ceramic materials have an index on the order of 2-3, thereby indicating a Brewster angle of 63° to 72°.

Several detector schemes have been studied in the past. One approach incorporating a total integrated scatter (TIS) measuring apparatus 20 shown in simplified schematic diagram form in FIG. 4 typically employs a He-Ne laser 22, an optical component 24 to filter the laser beam, a hemispherical collecting mirror 26 to collect the total scattered light over $2\pi$ steradians, and first and second detectors 28 and 30 to respectively detect direct scattered light and specularly scattered light. The TIS measuring apparatus 20 has been used to study surface finish and TIS as it relates to surface finish as expressed by the following equation:

$$TIS = \frac{V_s}{V_{s+\Delta s}} = \left(\frac{4\pi\delta}{\lambda}\right)^2 \quad [\text{Eq. 1}]$$

where
$V_s$ = Voltage of detector for scattered light only
$V_{s+\Delta s}$ = Voltage of detector for scattered light PLUS specularly scattered light δ = Surface roughness in rms.μm
λ = Wavelength of incident light.μm Another approach employing an angle-resolved scattering (ARS) measurement apparatus 32 shown in simplified schematic diagram form in FIG. 5 also includes a He-Ne laser 34. The ARS measurement apparatus 32 further includes such elements as a chopper 36, a polarizer 38 and a spatial filter 40 in the input optics to, among other things, set the polarization, and an analyzing polarizer 42 in the detector 48 which also includes a receiving telescope 44 and a lock-in amplifier 46. The detector 48 is mounted on a rotating stage to detect angular dependent scatter.

Another analytical approach to scattering distribution analysis is the Bi-direction Scatter Distribution Function (BSDF) first proposed by Nicodemus et al. in 1977. Variations of this function are BRDF, BTDF and BVDF for reflective, transmissive and volume scattering, respectively. All variations, however, are considered subsets of BSDF which is usually quantified in radiometric terms as the quotient of the scattered surface radiance divided by the incident surface radiance. Referring to FIG. 6, there is shown a schematic diagram illustrating the geometry used in defining BRDF, where the scattered surface radiance S is defined as the light flux (dp) scattered per unit surface area (A) per unit solid angle and is given as follows by Eq. 2.

$$\text{scattered surface radiance} = S = \frac{dp}{A} \cdot \frac{1}{\text{Projected solid angle}} \quad \frac{\text{watts}}{\text{mm}^2} \quad \text{Eq. 2]}$$

where
projected solid angle $= d\Omega_s \cdot \cos\theta_s$.

The incident surface irradiation is the light flux on the surface per unit of illuminated surface area and is expressed as $$\text{Incident surface irradiance} = I = \frac{Pi}{A} \text{ watts/mm}^2 \quad \text{Eq. 3]}$$

Thus, the BRDF is given by the following $$BRDF = \frac{S}{I} = \frac{dP/A}{Pi/A} \cdot \frac{1}{d\Omega_s \cos\theta_s} = \frac{1}{Pi}\left(\frac{dP}{d\Omega_s \cos\theta_s}\right) \quad \text{Eq. 4]}$$

Because the BRDF accounts for differences in reflected light, the BRDF will be modified as a function of the position of the analyzing polarizer and the type of scatterer.

In addition to the optical approaches to surface and subsurface defect detection and characterization described above, x-ray CT (computer tomography) scanning has also been used to detect defects in ceramic products. However, this technique suffers from limitations in detecting defects in the near-surface layer in curved or other complex shapes due to an averaging of the signal based on data from the sample and air. The image is formed from square pixels giving rise to irregular edges and limited spatial resolution. Recently, ultrasonics has been used for detecting surface and near-subsurface defects, but this approach is currently limited by coupling problems.

The present invention overcomes the aforementioned limitations of the prior art by providing a non-destructive method and apparatus for detecting surface and near-subsurface defects in dense ceramics and particularly in ceramic products with complex shapes such as ceramic bearings, turbine blades, races and the like.

OBJECTS AND SUMMARY OF THE INVENTION

Accordingly, it is an object of the present invention to detect surface and near-subsurface defects in ceramic bodies having appropriate optical transmittance properties using a laser beam.

It is another object of the present invention to provide for the non-destructive detection of potential spallation in dense structural ceramics such as ceramic rolling elements.

Yet another object of the present invention is to provide for the non-destructive testing of dense ceramic products particularly those having complex shapes such as bearings, turbine blades and races.

A further object of the present invention is to provide a highly accurate, optical method and apparatus for the non-destructive testing of dense ceramic bodies which may be employed as the ceramic bodies are produced for the detection of surface or near-subsurface defects.

A still further object of the present invention is to use Fourier optics in the detection and analysis of surface and subsurface defects in structural ceramic materials.

Still another object of the present invention to detect and analyze subsurface microdefects in ceramic materials using polarized electromagnetic radiation.

The present invention contemplates apparatus and method for the laser irradiation of a dense ceramic body for detecting surface and near-subsurface defects, and particularly in ceramic products with complex shapes such as ceramic bearings, turbine blades, races, and the like. The wavelength of the laser is selected in accordance with the optical characteristics of the ceramic sample, with the laser directed on the ceramic sample while the sample is stationary or rotated or translated, for detecting the presence of a signal due to a surface or near-subsurface defect. Where the ceramic sample is of $Si_3N_4$, one laser wavelength which functions is 6328 Å for helium neon light laser with total penetration being on the order of 750 μm. Accordingly, the layer being analyzed is approximately onehalf of the depth of penetration of the laser, exceeding 200 μm. By selecting a laser of a different wavelength, such as one in the infrared (IR) range, greater depths may be penetrated such as for testing the entire thickness of the sample. This invention may be used to detect surface and near-subsurface defects in a variety of ceramic products during production such as on-line detection of machining introduced damage for providing results quickly.

More specifically, this invention contemplates apparatus for detecting and characterizing surface and near-subsurface defects in a dense, light transmitting ceramic body, the apparatus comprising a source of incident polarized laser light and a lens for focusing the laser light on a surface of the ceramic body, whereby a portion of the laser light is scattered by the surface of the ceramic body and a portion of the laser light is transmitted by the ceramic body. An analyzing polarizer responsive to the scattered laser light measures changes in polarization between the incident and the scattered laser light, with a change in polarization of the laser light arising from scattering by a defect in the ceramic body. Use of Fourier optics in the detector system provides a method to determine characteristics of defects on the surface or subsurface in the ceramic body. The analyzing polarizer permits scattered light at a selected angle to be observed for enhancing sensitivity to either surface or near-subsurface defects.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIGS. 10a and 10b illustrate typical experimentally obtained optical Fourier transform scatter patterns obtained for: (a) ground and polished and (b) unidirectional ground only surfaces, respectively;

DETAILED DESCRIPTION OF THE PREFERRED EMBODIMENTS

Figure 1:
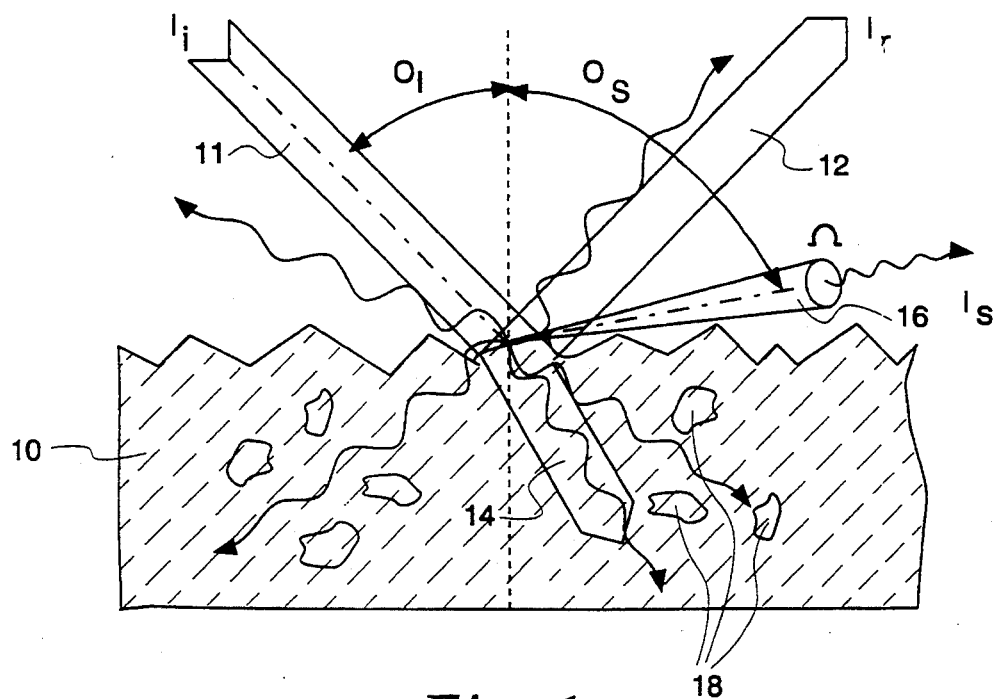
FIG. 1 is a simplified schematic diagram showing the optical scattering components for a semi-transparent polycrystalline ceramic.
Figure 2:
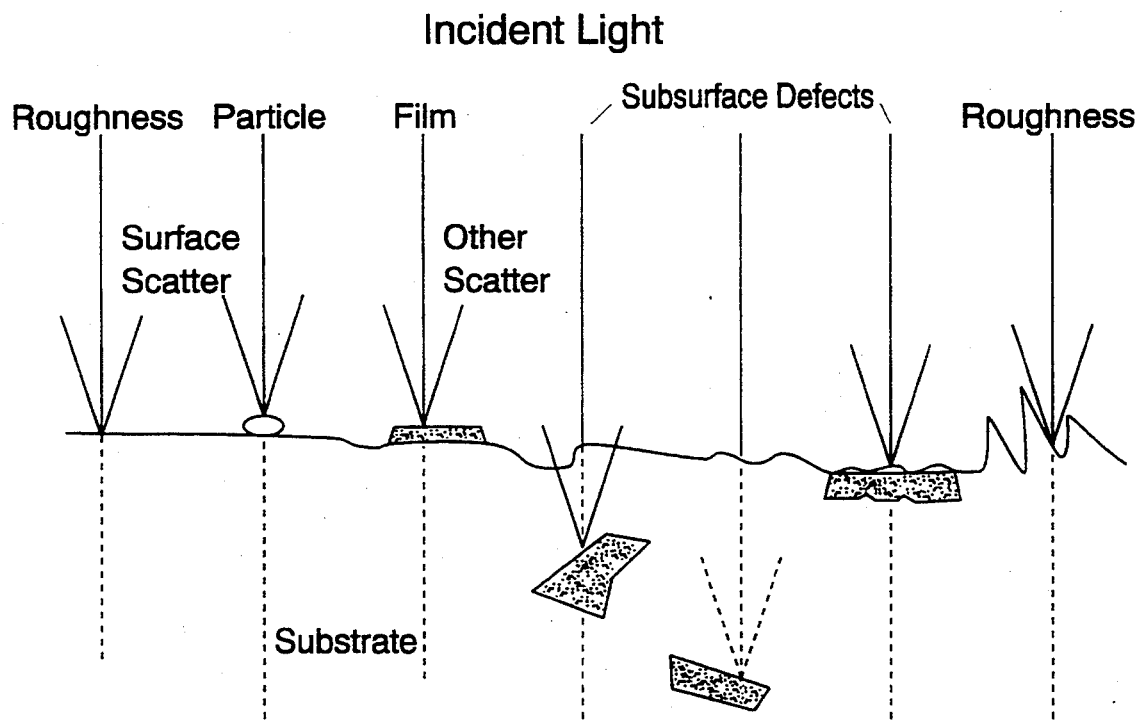
FIG. 2 is a schematic diagram showing different sources of optical scattering from a semi-transparent, or transparent, material including a range of surface roughness.
Figure 3:
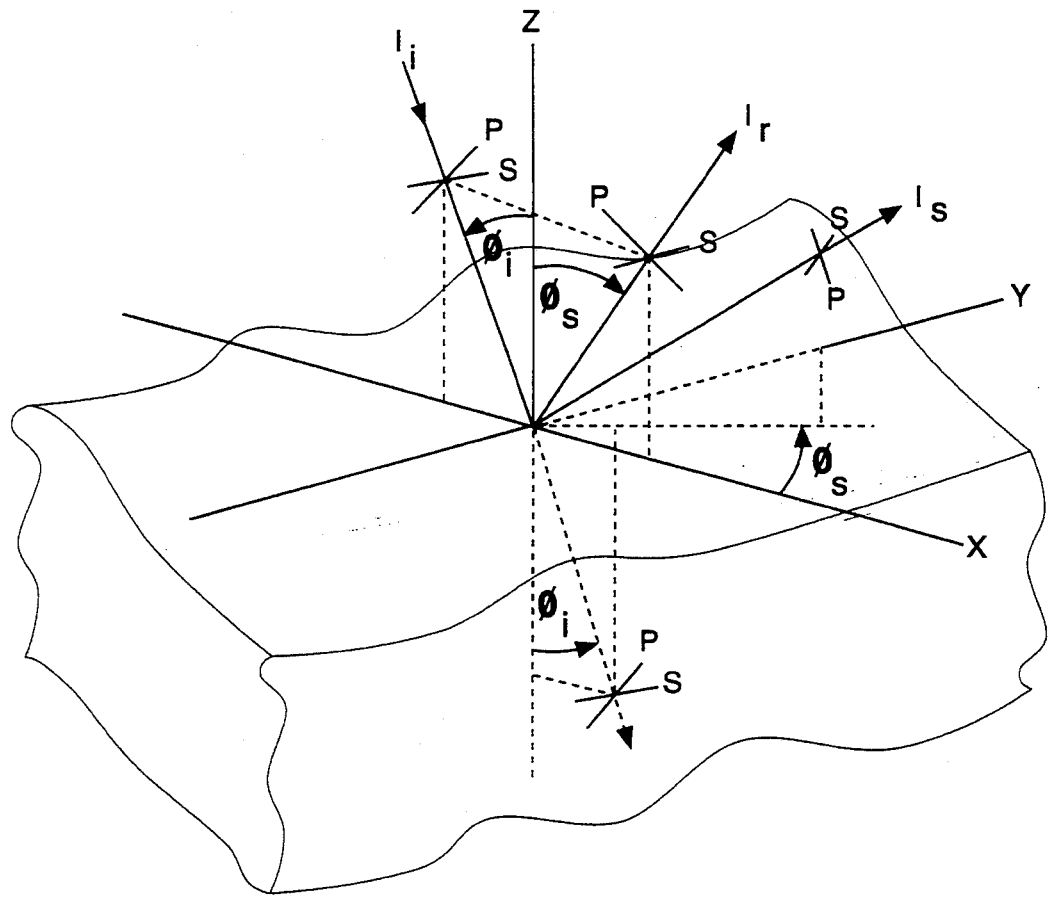
FIG. 3 is a schematic diagram showing polarization direction relative to the surface of a material irradiated by a polarized light beam.
Figure 4:
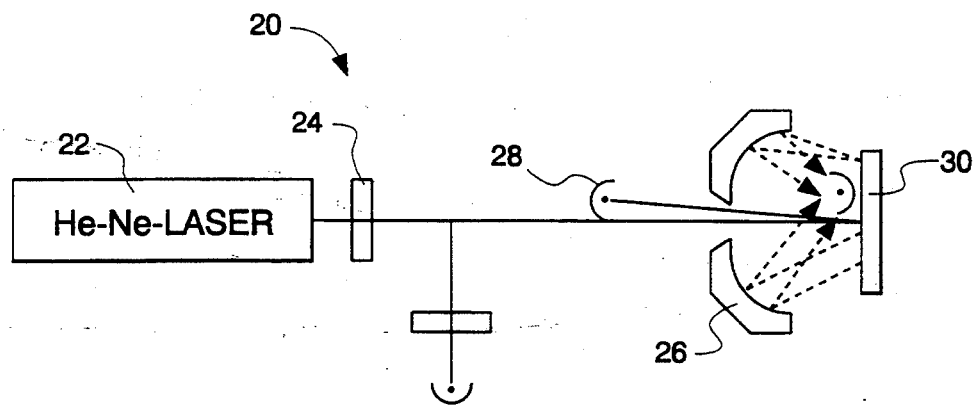
FIG. 4 is a simplified schematic diagram of the basic components of a prior art instrument for measuring total integrated scatter (TIS) from a sample.
Figure 5:
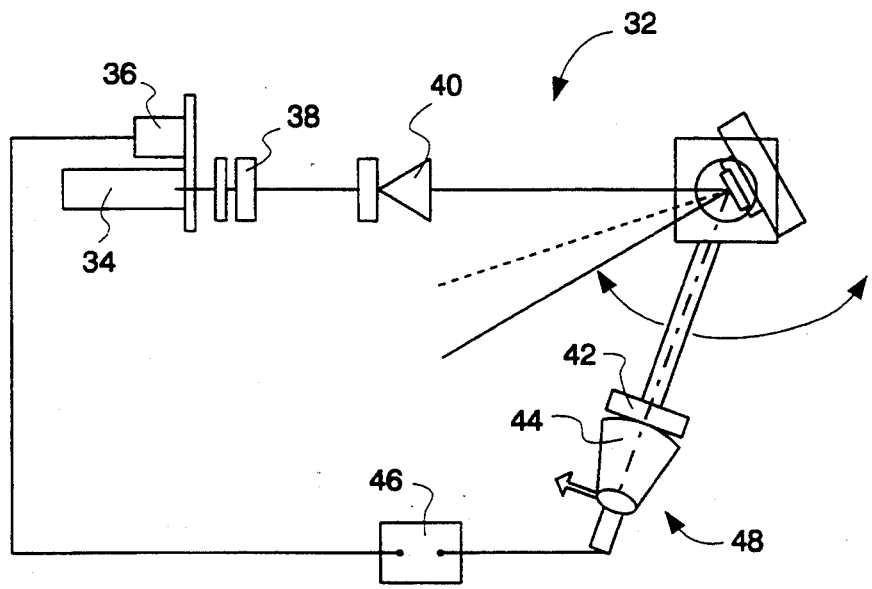
FIG. 5 is a simplified schematic diagram of the basic components of a prior art instrument for measuring angle-resolved scattering (ARS)
Figure 6:
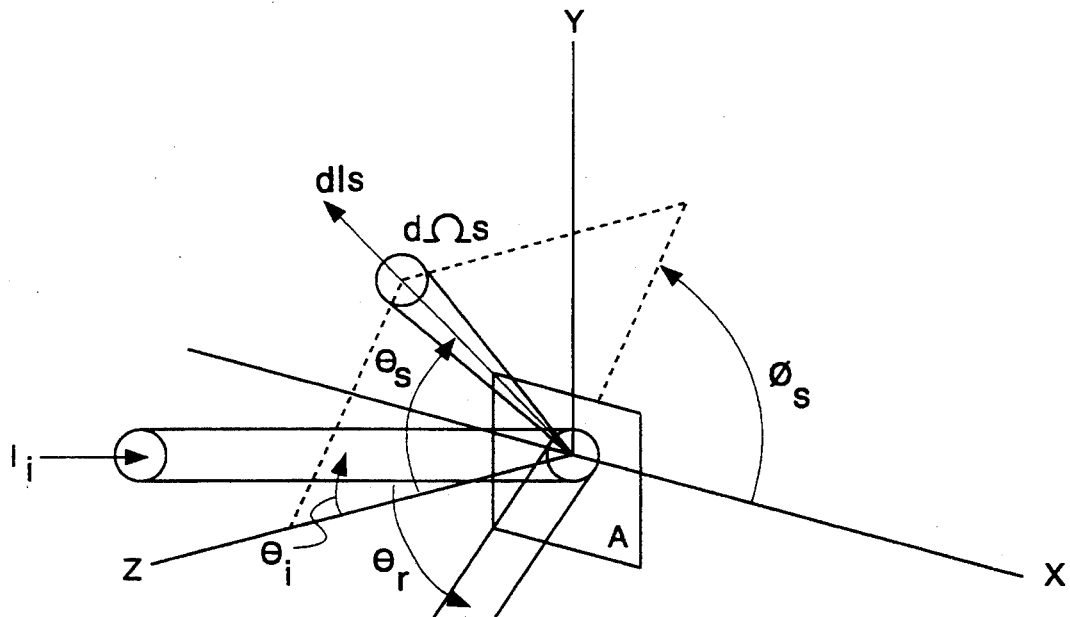
FIG. 6 is a schematic diagram showing the geometry used for defining the bi-directional reflective distribution function (BRDF)
Figure 7A:
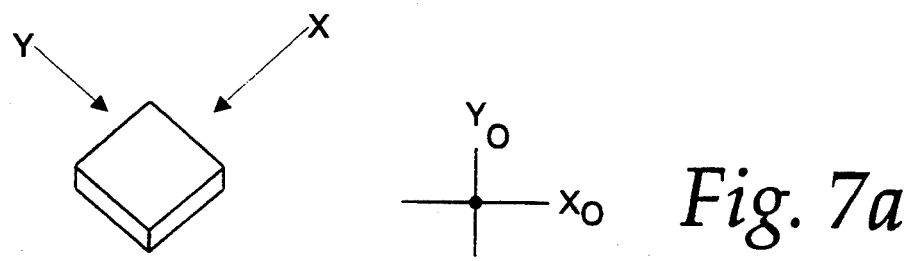
FIGS. 7a-7f are schematic diagrams showing the predicted two-dimensional Fourier transform plane of light scattered off of various surface types, such as: (a) perfect flat; (b) periodic; (c) periodic; (d) periodic; (e) random; and (f) periodic plus random.
Figure 7B:
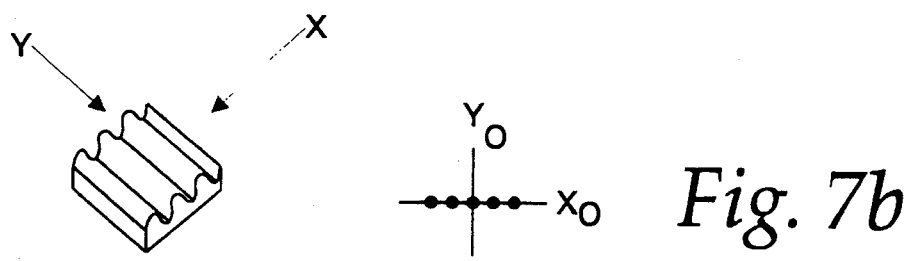
Figure 7C:
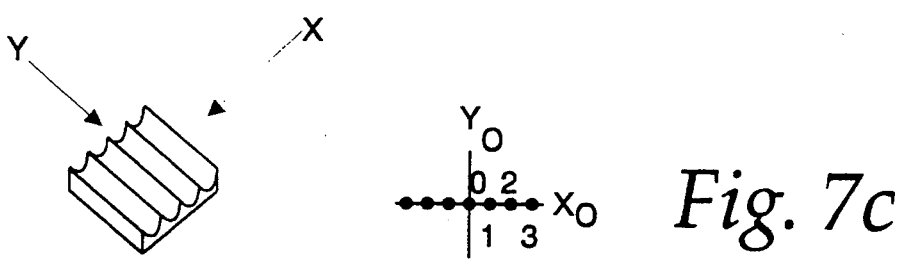
Figure 7D:
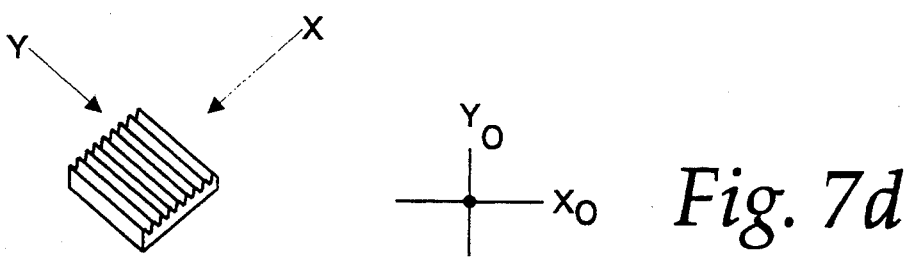
Figure 7E:
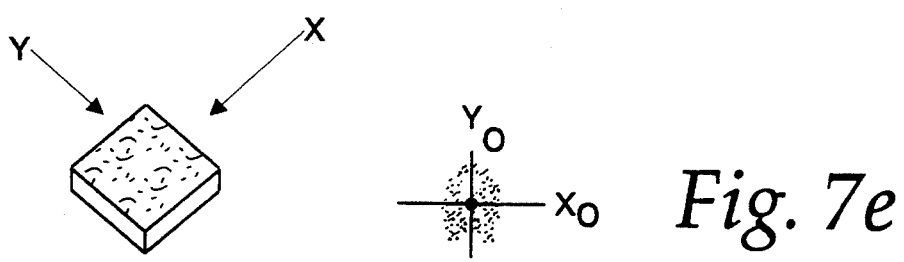
Figure 7F:
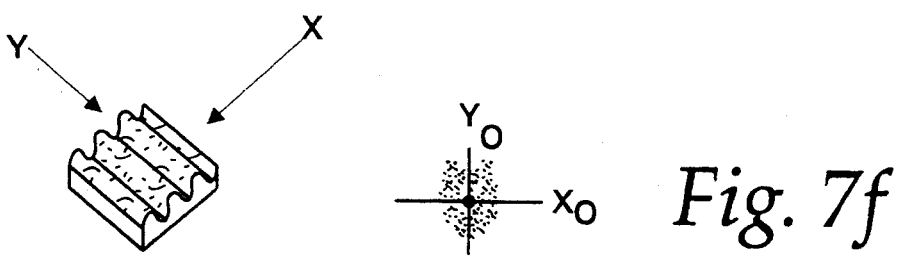
Figure 8:
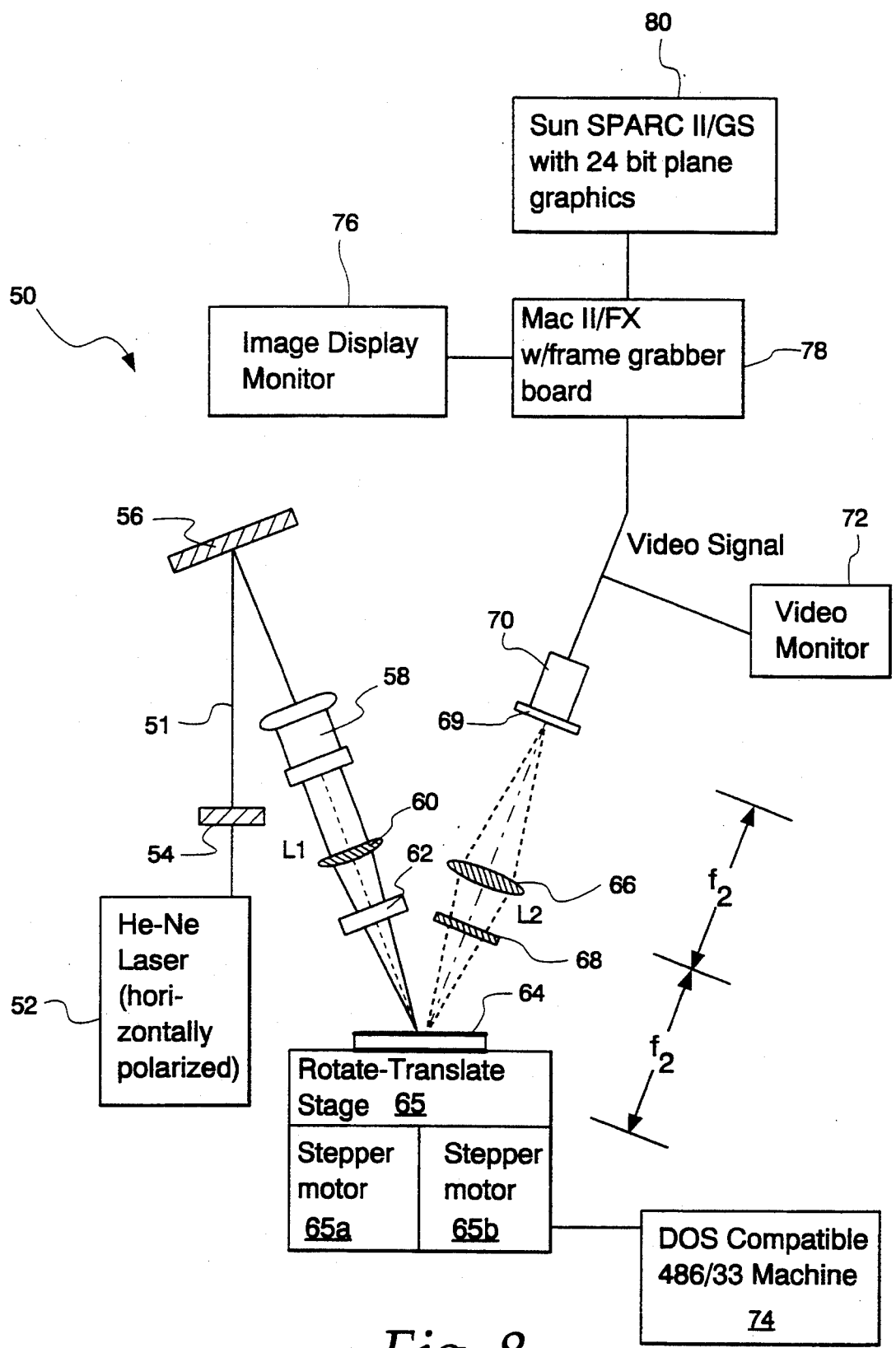
FIG. 8 is a schematic diagram of an optical system for detecting and characterizing surface and subsurface defects in a dense ceramic body in accordance with the principles of the present invention.

Referring to FIG. 8, there is shown a schematic diagram of a surface and near-subsurface defect detector 50 for use with optically transmitting materials such as dense ceramics. A source of laser light 52, whose wavelength is selected based on the optical properties of the ceramic, directs a polarized 35 mw laser beam 51 through a polarization rotator 54 in the form of a calibrated, ¼ wave plate and onto a planar mirror, or reflector, 56. The polarization rotator 54 provides polarized light at selected angles. Mirror 56 reflects the laser beam 51 through a combination spatial filter/collimater 58, which includes a spatial filter with a 6.3 μm pinhole and a 24 mm collimater, employed with a 95 cm focal length plano-convex lens 60 to focus the light to a spot on a ceramic test piece 64. An aperture 62 is interposed intermediate to plano-convex lens 60 and the ceramic test piece 64, with the laser beam focused to a spot size of approximately 1 mm in diameter. Defect detector 50 further includes a 110 mm diameter, 155 mm focal length double convex optical Fourier transforming lens 66 for focusing the laser light scattered by the ceramic test piece 64 onto an image display plate 69 coupled to a 512×512 charge couple device (CCD) array television camera 70 coupled to a lens with remotely controllable zoom and iris. Defect detector 50 further includes a video monitor 72 coupled to CCD camera 70. A rotating analying polarizer 68 is interposed between the sample and the optical Fourier lens 66 and the image display plate 69 for measuring the polarization change experienced by the scattered laser beam when scattered by the ceramic test piece 64. The output of the CCD camera 70 is coupled to an 8-bit analog-to-digital (A/D) board (not shown) in a MAC II/FX computer 78 which is loaded with National Institutes of Health (NIH) written image processing software modified in a conventional manner in order to handle digital image subtraction. The computer 78 is coupled to and drives an image display monitor 76. Computer 78 is connected to a Sun SPARC II/GS workstation with 24-bit plane graphics.

The ceramic test piece 64 is mounted on a UNIDEX rotate-translate stage 65 equipped with at least two stepper motors 65a and 65b and is controlled by a DOS compatible 486/33 computer 74. The ceramic test piece 64 can be translated at a constant incidence angle or may be rotated to change incidence (enhance reflection) angle. Although the optical detector system 50 is mounted on a 4'×8'×1' solid granite vibration isolated optical bench (not shown), it was found to be unnecessary to isolate the optical table.

After each ceramic test piece 64 was mounted to the rotate/translate stage 65 for analysis, the analyzing polarizer 68 was set such that almost total extinction of light reaching the image display medium 69 occurred. This angle changed slightly (<1°) with each surface finish type of the ceramic test piece 64. Four to six optical Fourier transform images were taken at locations on the ceramic test pieces away from the defects formed in the ceramic test pieces. These images were then averaged in computer 78 with the averaged data stored in the computer's memory. Image analysis software in the computer 78 allowed for image subtraction of "live video" from the CCD camera 70. Thus, as the specimen was translated and/or rotated and subsequent images were displayed on the image display monitor 76, if these images did not deviate from the "average image" substantially, the results were a blank (or totally dark) image on the monitor. However, if any subsequent image deviated from the "average image" greater than the predetermined, or stored, limits of the detection system, only the "difference image" was presented on video monitor 72. Thus, image display monitor 76 provides for the real-time monitoring of the level of the video signal from the CCD camera 70 to avoid video display saturation, while the "difference image" is presented on video monitor 72. Such "difference images" were obtained by step-wise scanning each ceramic test piece, with the size of each step varied from 50 $\mu$m to over 1 mm by the rotate-translate stage 65. By using this method, and digitally storing scanned images, analysis of the difference images by digital image processing methods were performed. This consisted primarily of gray-scale histogram analysis to establish differences in the images used to establish defect detection sensitivity. The analyzing polarizer 68 may be set to pass only light at a selected polarization angle for enhancing sensitivity to either surface or near-subsurface defects.

In order to determine initial optical transmission properties necessary for use with the optical detector system 50, step wedges of specimens under analysis, which in the present case were NBD 200 and Toshiba $Si_3N_4$, with step thicknesses of 100, 200, 400 and 600 $\mu$m were used with laser light having a wavelength of 0.6328 $\mu$m. These results demonstrated sufficient optical transmission to permit subsurface defect detection.

Figure 9A:
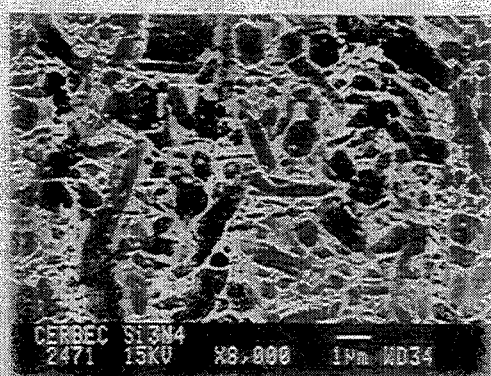
FIGS. 9a and 9b are photos showing the micro structure of Cerbec NBD200 and Toshiba $Si_3N_4$, respectively.
Figure 9B:
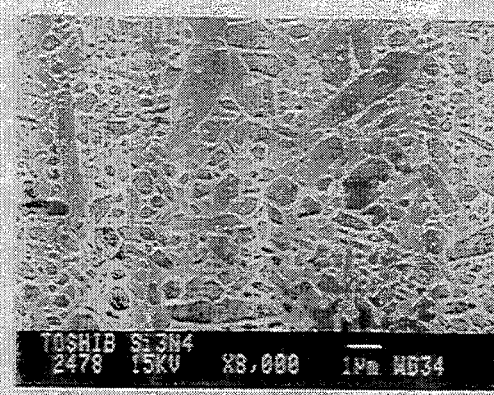

The microstructure of NBD 200 and Toshiba $Si_3N_4$ materials are respectively shown in the photographs of FIGS. 9a and 9b. Although these photographs show that each of these materials has a different microstructure, it is to be noted that each material has quite elongated grains of 3–5 $\mu$m and grains with diameters of up to 1 $\mu$m. Although often quoted as having less than 0.5 $\mu$m grain size by some producers, the $Si_3N_4$ grains have high aspect ratios and these microstructures need to be well defined for light scattering studies especially for subsurface defect detection.

All data reported below was obtained using an incidence angle (off surface normal) of 20°. This incident angle is not a limitation of the present invention, but was the smallest angle achievable with the equipment used in the optical detector system 50 shown in FIG. 8. Experimentally obtained optical Fourier scatter patterns were obtained on all specimens and were similar to the theoretically predicted patterns for randomly rough surfaces or for uni-directional roughened surfaces. Typical patterns obtained for both a ground and polished specimen (Ra=0.03 $\mu$m) and a uni-directional ground specimen (Ra=0.07 $\mu$m) are respectively shown in FIGS. 10a and 10b.

MOR bars 3×5×25 mm of both NBD 200 and Toshiba $Si_3N_4$ were used for the ceramic test piece 64 in the optical detector system 50 of the present invention for providing the results described herein. The MOR bars were machined using either a grinding procedure or a grinding procedure followed by polishing. Four NBD 200 bars and four Toshiba bars were produced and analyzed for surface and near-subsurface defects. Two of each type of bar were ground and polished, while the remaining two of each type of bar were ground only. In each group, ground and polished or ground only, ultrasonically drilled non-through holes 1.5 mm in diameter were drilled perpendicular to the machined surface, but on the opposite side of the test specimen. Thus, the machined surface appeared defect-free. A series of two to four holes approximately 2–4 mm apart were drilled such that the defect depth below surface ranged from 50–200 $\mu$m. Similarly, slots were cut on the MOR bars such that 50–200 $\mu$m of material remained between the slot and the specimen's upper surface.

Figure 11A:
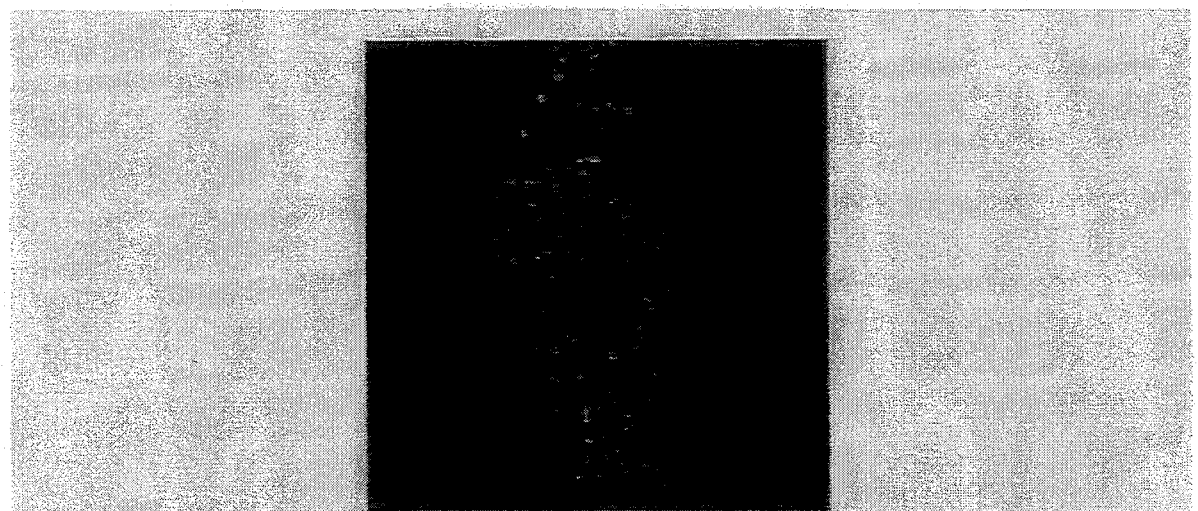
FIGS. 11a, 11b and 11c respectively illustrate typical Fourier/transform difference images experimentally obtained on Cerbec ground and polished specimens containing: (a) no defects; (b) a 75 μm deep defect; and (c) a 102 μm deep defect.
Figure 11B:
Figure 11C:
Figure 11D:
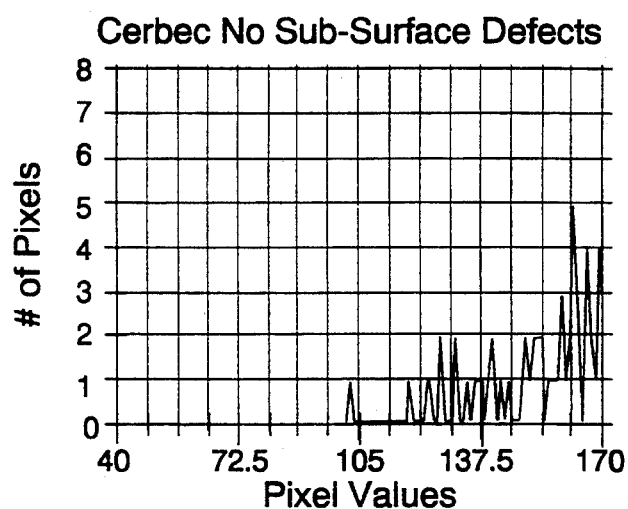
FIGS. 11d, 11e and 11f illustrate typical histograms of the gray scale values of the total difference images for the Fourier transform difference images respectively shown in FIGS. 11a, 11b and 11c.
Figure 11E:
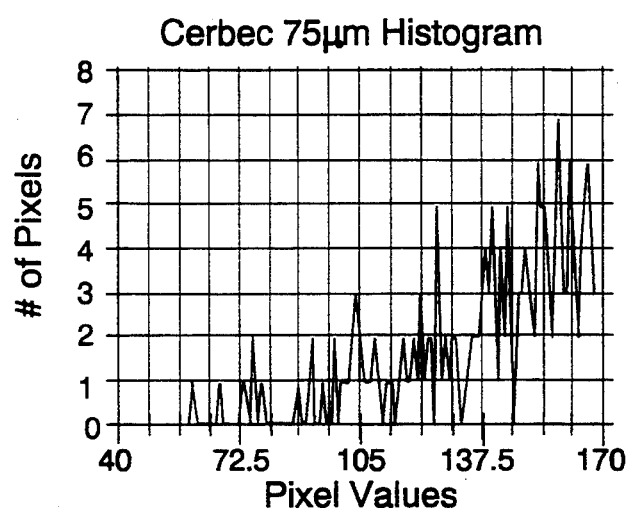
Figure 11F:
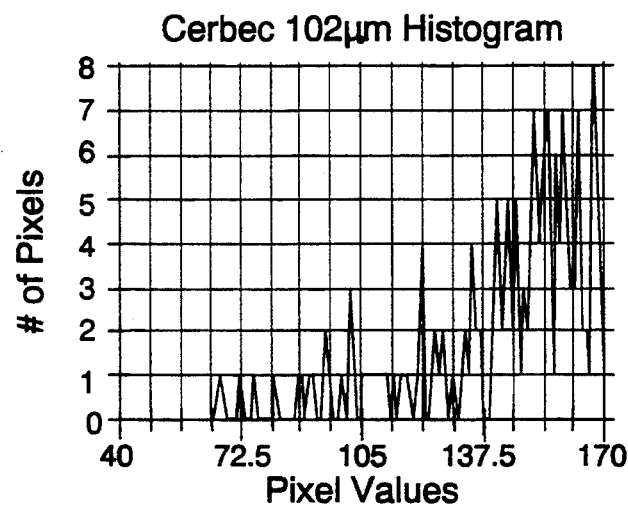

For drilled hole synthesized subsurface defects using the "difference image" method, 75 and 105 $\mu$m deep defects could be easily detected in either the ground and polished or ground ceramic test specimens. This is observable in real-time during live video subtraction and is verified by histogram analysis. Typical examples of the optical analysis of a ceramic test specimen are shown in FIGS. 11a, 11b and 11c for test specimens respectively having: (a) no defects; (b) a 75 $\mu$m deep defect; and (c) a 102 $\mu$m deep defect in a ground and polished Cerbec specimen. It should be noted that in these difference images the "no defect image" is not totally black. This is thought to be caused by local differences in microstructure as noted in FIGS. 9a and 9b. Microstructure differences may give rise to changes in scattered light polarization which would then pass the analyzing polarizer and be detected. For synthesized defects, a different scatter pattern is observed. The differences are manifested in both a large number of high intensity components (intensity of white spots) and Fourier component distribution as shown in FIGS. 11b and 11c. Quantification of these differences is shown in FIGS. 11d, 11e and 11f which include typical histograms of the gray scale values of the resulting total difference images for a ceramic test specimen having (a) no defects; (b) a 75 $\mu$m deep defect; and (c) a 102 $\mu$m deep defect, respectively. In analyzing these histograms, the number of pixels with intensity values less than 138 (0 is white, 255 is black) is noted. The reason for this is that lower gray scale values indicate the presence of higher quantities of light passing through the analyzing polarizer than the no defect average image. Thus, significant differences between the 75 $\mu$m deep defect and the 102 $\mu$m deep defect are observed. This is as expected because of the more significant attenuation (scatter) for deeper defects. Further, detailed analysis of the difference images of FIGS. 11a, 11b and 11c reveals that the higher spatial frequency components of the 102 $\mu$m deep defect have less intensity than the high spatial frequency components of the 75 $\mu$m deep defect. Thus, analysis of these components may provide a method to establish depth sensitivity. Similar results were obtained for the Toshiba $Si_3N_4$ ground and polished test specimens.

Figure 12A:
FIGS. 12a, 12b and 12c illustrate typical Fourier transform difference images experimentally obtained on Cerbec ground specimens for: (a) no defects; (b) a defect at 75 μm depth; and (c) a defect at 102 μm depth.
Figure 12B:
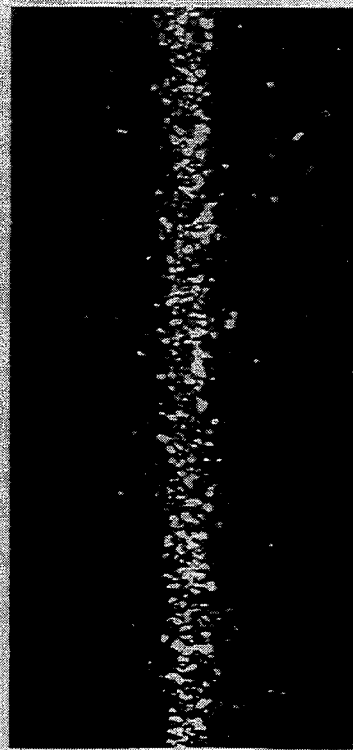
Figure 12C:
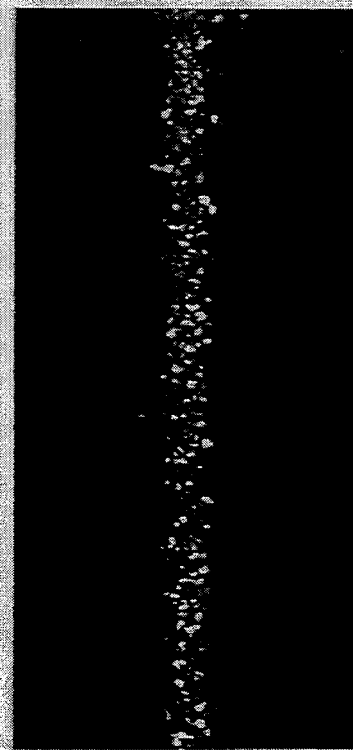
Figure 12D:
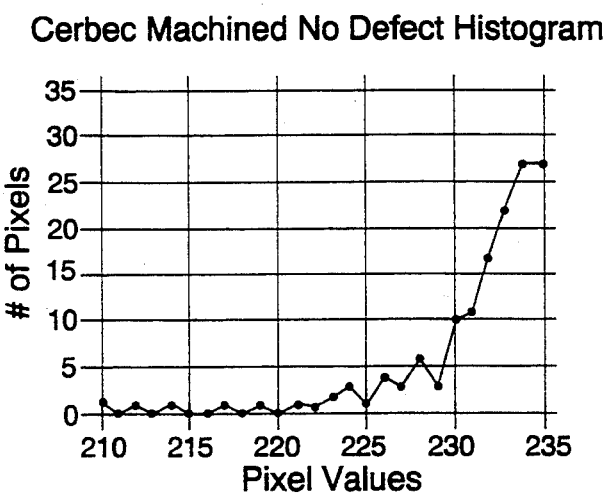
FIGS. 12d, 12e and 12f respectively illustrate the histograms of gray scales of the optical Fourier difference images for a test specimen having: (a) no defects; (b) a 75 μm deep defect; and (c) a 102 μm deep defect.
Figure 12E:
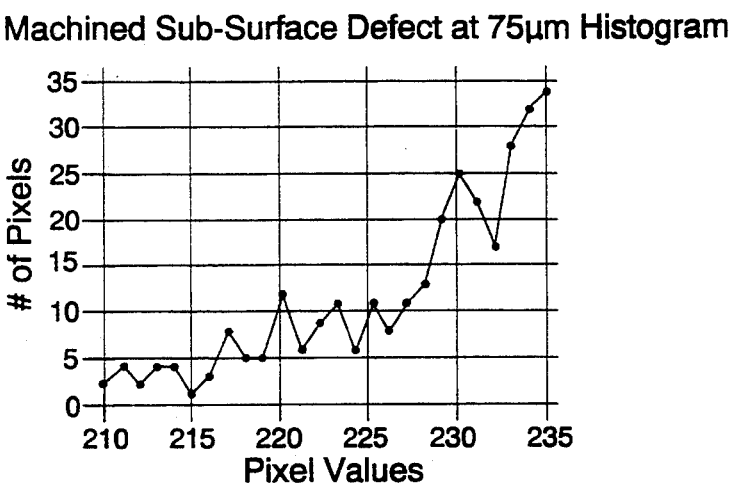
Figure 12F:
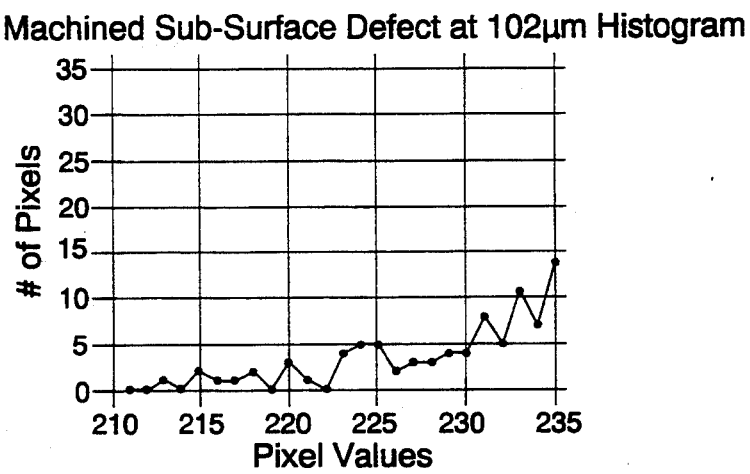

Referring to FIGS. 12a, 12b and 12c there are respectively shown the optical Fourier transform difference images for the Cerbec ground specimen (Ra=0.07 $\mu$m) for: (a) no defects; (b) a 75 $\mu$m deep defect; and (c) a 102 $\mu$m deep defect. As with the ground and polished specimens, distinct high frequency components with much greater intensity (brightness) are observed for regions of the bar with a defect than without a defect. In addition, the intensity is higher for the 75 $\mu$m deep defect than for the 102 $\mu$m deep defect, which result is quantified in FIGS. 12d, 12e and 12f. FIGS. 12d, 12e and 12f respectively illustrate the histograms of gray scales of the optical Fourier difference images for a test specimen having: (a) no defects; (b) a 75 $\mu$m deep defect; and (c) a 102 $\mu$m deep defect. The highest brightness is again observed for the 75 $\mu$m deep defect. For the synthesized crack defect specimens, the edge of the cut could be detected by scatter using the optical detector system 50 of FIG. 8.

As shown in FIG. 8, the optical Fourier transforming lens 66 has a front focal plane located at the ceramic test piece 64 and a back focal plane located at the image display medium 69. Fourier optics yields a two-dimensional Fourier transform at the back focal plane of the double convex optical Fourier transforming lens 66. By selecting the scatter pattern by means of the analyzing polarizer 68 and by looking at the back focal plane (or Fourier transform plane), characteristics of features within the ceramic test piece may be represented in two-dimensions, where spatially distributed features are represented by light intensity and position. Large features in the ceramic will be identified by the presence of intensity patterns more closely spaced corresponding to a lower frequency content. Smaller features will be identified by intensity patterns with components spaced further apart corresponding to a higher frequency content. Two-dimensional Fourier optics thus can provide information relating to the size, location and characteristics of features in a body, or reference frame, having length, width and depth provided that each dimension effects the scatter characteristics. The intensity (brightness) and location of the optical Fourier components at the back focal plane, i.e., at the image display medium 69, provide information relating to the scattering components.

There has thus been shown an optical method and apparatus for detecting surface and near-subsurface defects in a dense ceramic. Using a hybrid cross-polarization technique and Fourier optics analysis, defects as deep as 200 μm can be detected and presented on an image display monitor. Polarized laser light directed onto the ceramic test piece is scattered from the surface and subsurface defects. The scattered light polarization angle will be different than the polarization angle of the incident laser beam. P polarization angle is used to separate surface and subsurface defects. By storing known "feature masks" in the computer representing defects having a range of sizes and location depths from the surface, defects can be automatically characterized by comparing the detected scatter pattern with the known feature masks. The invention is particularly useful in detecting and characterizing surface and subsurface defects in structural ceramic bodies having an irregular shape such as bearings, turbine blades and races.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. Apparatus for detecting and characterizing surface and near-subsurface defects in a dense, light transmitting ceramic body, said apparatus comprising: a source of incident polarized laser light; a lens for focusing said laser light on a surface of the ceramic body, whereby a portion of said laser light is scattered by the surface of the ceramic body and a portion of said laser light is transmitted by the ceramic body and is scattered by a subsurface portion of the ceramic body; an analyzing polarizer responsive to the scattered laser light for measuring a change in polarization between said incident and said scattered laser light, wherein a change in polarization of said scattered laser light is caused by a defect in the ceramic body; optical Fourier transform means responsive to said scattered laser light for providing a two-dimensional display of the characteristics of defects in the ceramic body; and means for measuring an average image of the ceramic body without the presence of defects and for comparing the scattered laser light with said average image for displaying a difference image representing defects in the ceramic body.

2. The apparatus of claim 1 wherein said source of polarized laser light includes a He-Ne laser in combination with a polarization rotator for establishing said polarization.

3. The apparatus of claim 2 wherein said polarization rotator comprises a ½ wave plate.

4. The apparatus of claim 2 wherein said incident polarized laser light has a wavelength of 6328 Å.

5. The apparatus of claim 2 wherein said polarization rotator provides P polarized incident laser light for detecting subsurface defects in the ceramic body.

6. The apparatus of claim 2 wherein said polarization rotator provides S polarized incident laser light for detecting surface defects in the ceramic body.

7. The apparatus of claim 1 further comprising rotating means coupled to the ceramic body for rotationally displacing the ceramic body while irradiated by said incident polarized laser light.

8. The apparatus of claim 1 further comprising translating means coupled to the ceramic body for translationally displacing the ceramic body while irradiated by said incident polarized laser light.

9. The apparatus of claim 1 wherein said analyzing polarizer separates surface and subsurface scattered light.

10. The apparatus of claim 1 wherein said analyzing polarizer is responsive to scattered light at a selected polarization for enhancing sensitivity of said apparatus to either surface scattered light or near-subsurface scattered light.

11. A method for detecting and characterizing surface and near-subsurface defects in a dense, light transmitting ceramic body, said method comprising:
   providing laser light with a given polarization;
   directing said laser light on a surface of the ceramic body, wherein said laser light enters the ceramic body and is scattered by surface and near-subsurface defects in the ceramic body;
   measuring a change in polarization of said laser light arising from scattering of said laser light by defects in the ceramic body; and
   visually displaying the measured change in polarization of said laser light representing characteristics of the defects by Fourier transforming the measured change in polarization to a frequency domain; and
   measuring the laser light transmitted through a portion of the ceramic body without any defects, and wherein the step of visually displaying the measured change in polarization includes comparing defect scattered laser light with laser light scattered from a portion of the ceramic body without any defects for visually displaying a difference image.

12. The method of claim 11 wherein the step of providing laser light with a given polarization includes directing a laser beam through a ½ wave polarization rotator plate.

13. The method of claim 11 further comprising the step of rotating the ceramic body while said laser light is directed on the surface thereof.

14. The method of claim 11 further comprising the step of translating the ceramic body while said laser light is directed on the surface thereof.

15. The method of claim 11 further comprising the step of directing laser light scattered by defects in the ceramic body to a video camera including the step of limiting the laser light scattered by defects to almost total extinction prior to reaching said video camera.

16. The method of claim 11 further comprising the step of storing an average image representing the laser light scattered from a ceramic body and not scattered by defects and comparing the scattered laser light with said average image for displaying a difference image representing the location and characteristics of defects on the ceramic body.

17. The method of claim 11 further comprising the step of measuring a change in polarization of either P polarized incident laser light for increasing sensitivity to subsurface scattered light or S polarized incident laser light for increasing sensitivity to surface scattered light.

* * * * *

UNITED STATES PATENT AND TRADEMARK OFFICE
CERTIFICATE OF CORRECTION

PATENT NO. : 5,426,506
DATED : June 20, 1995
INVENTOR(S) : William A. Ellingson and Mark P. Brada It is certified that error appears in the above-indentified patent and that said Letters Patent is hereby corrected as shown below:

In column 6, line 30, change "analying" to -- analyzing --.

In column 5, line 52, delete the "/" between the words "Fourier and transform".

Signed and Sealed this

Nineteenth Day of September, 1995

Attest:

BRUCE LEHMAN

Attesting Officer    Commissioner of Patents and Trademarks